(12) United States Patent
Keller et al.

(10) Patent No.: US 11,737,918 B2
(45) Date of Patent: Aug. 29, 2023

(54) SUCTION CUP DESIGN FOR CAPSULOTOMY DEVICE

(71) Applicant: Centricity Vision, Inc., Fremont, CA (US)

(72) Inventors: Christopher Guild Keller, El Cerrito, CA (US); David Wong Manhin Sretavan, Tiburon, CA (US)

(73) Assignee: CENTRICITY VISION, INC., Fremont, CA (US)

( * ) Notice: Subject to any disclaimer, the term of this patent is extended or adjusted under 35 U.S.C. 154(b) by 200 days.

(21) Appl. No.: 17/112,759

(22) Filed: Dec. 4, 2020

(65) Prior Publication Data
US 2022/0079810 A1 Mar. 17, 2022

Related U.S. Application Data

(60) Provisional application No. 63/078,128, filed on Sep. 14, 2020.

(51) Int. Cl.
*A61F 9/007* (2006.01)

(52) U.S. Cl.
CPC .... *A61F 9/00754* (2013.01); *A61B 2217/005* (2013.01)

(58) Field of Classification Search
CPC ............. A61F 9/00754; A61F 9/00736; A61B 2217/005
See application file for complete search history.

(56) References Cited

U.S. PATENT DOCUMENTS

| | | | |
|---|---|---|---|
| 2007/0191862 A1 | 8/2007 | Ellis | |
| 2011/0071524 A1 | 3/2011 | Keller | |
| 2013/0197548 A1 | 8/2013 | Keller | |
| 2015/0216728 A1* | 8/2015 | Keller | A61B 18/082 606/45 |
| 2016/0354245 A1* | 12/2016 | Horvath | A61F 9/0017 |
| 2018/0271704 A1 | 9/2018 | Lifshitz et al. | |
| 2019/0231593 A1 | 8/2019 | Keller et al. | |

FOREIGN PATENT DOCUMENTS

| | | |
|---|---|---|
| DE | 7414422 U | 9/1974 |
| FR | 2375004 A1 | 7/1978 |

OTHER PUBLICATIONS

PCT International Search Report and Written Opinion, PCT Application No. PCT/US21/45462, dated Nov. 30, 2021, 18 pages.

* cited by examiner

*Primary Examiner* — Sarah A Simpson
*Assistant Examiner* — Raihan R Khandker
(74) *Attorney, Agent, or Firm* — Fenwick & West LLP

(57) ABSTRACT

A device is described herein for performing capsulotomies that improves suction uniformity and produces rolled capsulotomy edges. The device includes a suction cup that forms a tapered circumferential suction chamber which enables suction to be applied to a tissue in a first direction. The tapered circumferential suction chamber decreases in cross-sectional area from a proximal end of the device towards a distal end of the device. The device further includes a stem coupled to the suction cup to provide suction to the suction cup. The stem forms a neck that enables fluid flow to the suction cup in a direction substantially perpendicular to the first direction. The device further includes a cutting element configured to excise the tissue.

13 Claims, 13 Drawing Sheets

SUCTION CUP DESIGN FOR CAPSULOTOMY DEVICE

CROSS-REFERENCE TO RELATED APPLICATION

This application claims the benefit of provisional U.S. Patent Application No. 63/078,128, filed on Sep. 14, 2020, which is incorporated by reference herein in its entirety for all purposes

BACKGROUND

This description generally relates to medical devices and specifically to microsurgical instruments for capsulotomies.

Current tissue cutting devices frequently cause uneven suction, which can lead to inadequate capsule cutting. Uneven suction is particularly problematic for tissue cutting devices that deliver suction to a suction cup through a single orifice located at one peripheral location of the suction cup. Further, current tissue cutting devices frequently create inconsistent edges in the cut tissue, which may not be strong enough to endure the remaining steps of a cataract surgery. Further, using current tissue cutting devices, alignment of the center of the device with a desired surgical landmark is difficult. Finally, using current tissue cutting devices, it is difficult to visually monitor the suction level inside the device.

SUMMARY

Embodiments relate to a microsurgical device for tissue cutting that produces consistent capsulotomies and improves upon current tissue cutting devices. The microsurgical device provides even suction throughout the circumference of the suction cup and produces strong rolled edges that are tear resistant. Further, the microsurgical device consistently produces complete capsulotomies without residual tags attached to a capsulotomy edge. In addition, the device may include features that assist a surgeon during device placement, allow visual monitoring of the amount of suction developing in the suction cup, or the like.

The design of the suction cup ensures uniform suction is applied to tissue being excised. For example, the suction cup may form a tapered circumferential suction chamber which decreases in cross-sectional area from a proximal end of the device towards a distal end of the device. In addition, a central portion of the suction cup may have a shorter height than a circumferential portion, such as the tapered circumferential suction chamber, of the suction cup. By having tapered circumferential suction chamber and/or a shorter central portion, the amount of material to be evacuated under suction is reduced, ensuring more uniform suction. Further, in some embodiments, the suction cup may include one or more standoffs that create channels for material flow. Due to the channels formed, uniform suction is developed throughout the suction cup.

In addition to the design of the suction cup, the configuration of the stem coupled to the suction cup ensures uniform suction is applied to the tissue being excised. Suction is applied to the suction cup through an orifice of a stem coupled to a tapered side of the suction cup. In some embodiments, a neck of the stem enables fluid flow to and from the stem into the suction cup in a direction substantially perpendicular to the direction of suction being applied to the tissue. For example, fluid flow through the neck may be substantially horizontal and the suction force applied to the tissue may be substantially perpendicular. The different flow directions help ensure uniform suction is applied to the tissue.

Further, the configuration of the suction cup helps to ensure consistent rolled edges are formed. The suction cup is configured to ensure that only a portion of the cutting element is in physical contact with the tissue being excised. For example, in some embodiments, only an inner bottom edge of the cutting element comes into physical contact with a tissue being excised. The outer bottom edge of the cutting element is physically isolated from the tissue but is located at a sufficient distance from the tissue to remotely affect the tissue via a temperature change. The temperature change assists in the creation of a rolled edge.

In addition, manufacturing, transport, and use of the device are eased by the design of the suction cup. For example, the suction cup may include a containment pocket that is collapsible between horizontal and vertical positions. The containment pocket may be molded in a vertical position and assembled and/or transported in a horizontal position. Further, different portions of the suction cup may have various thicknesses to reduce the amount of material used in the suction cup. By reducing the amount of material in the suction cup, the force needed to insert the suction cup through an incision is reduced.

The figures depict various example embodiments of the present technology for purposes of illustration only. One skilled in the art will readily recognize from the following description that other alternative embodiments of the structures and methods illustrated herein may be employed without departing from the principles of the technology described herein.

DETAILED DESCRIPTION

Figure 1A:
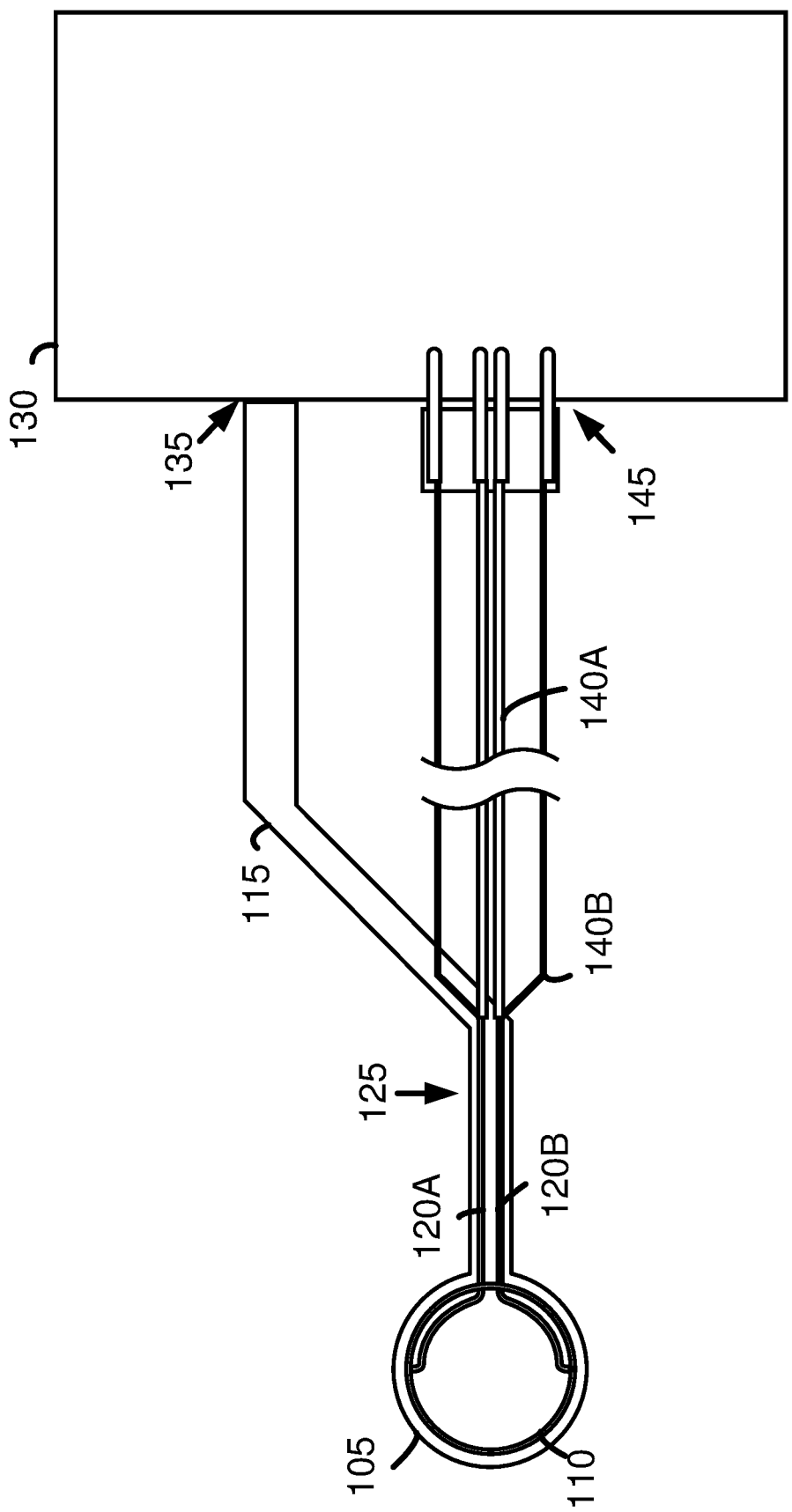
FIG. 1A illustrates a microsurgical device connected to its control console, according to one embodiment.
Figure 1B:
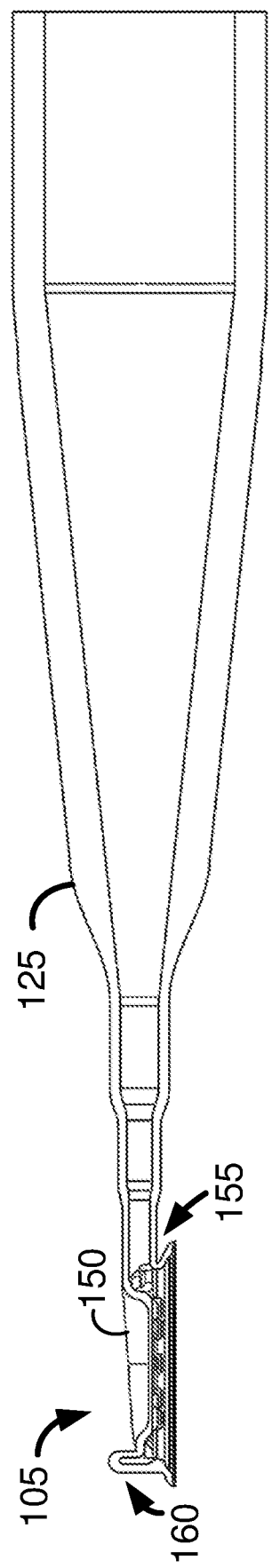
FIGS. 1B-1C illustrate cross-sectional views of the microsurgical device shown in FIG. 1A, according to one embodiment.
Figure 1C:
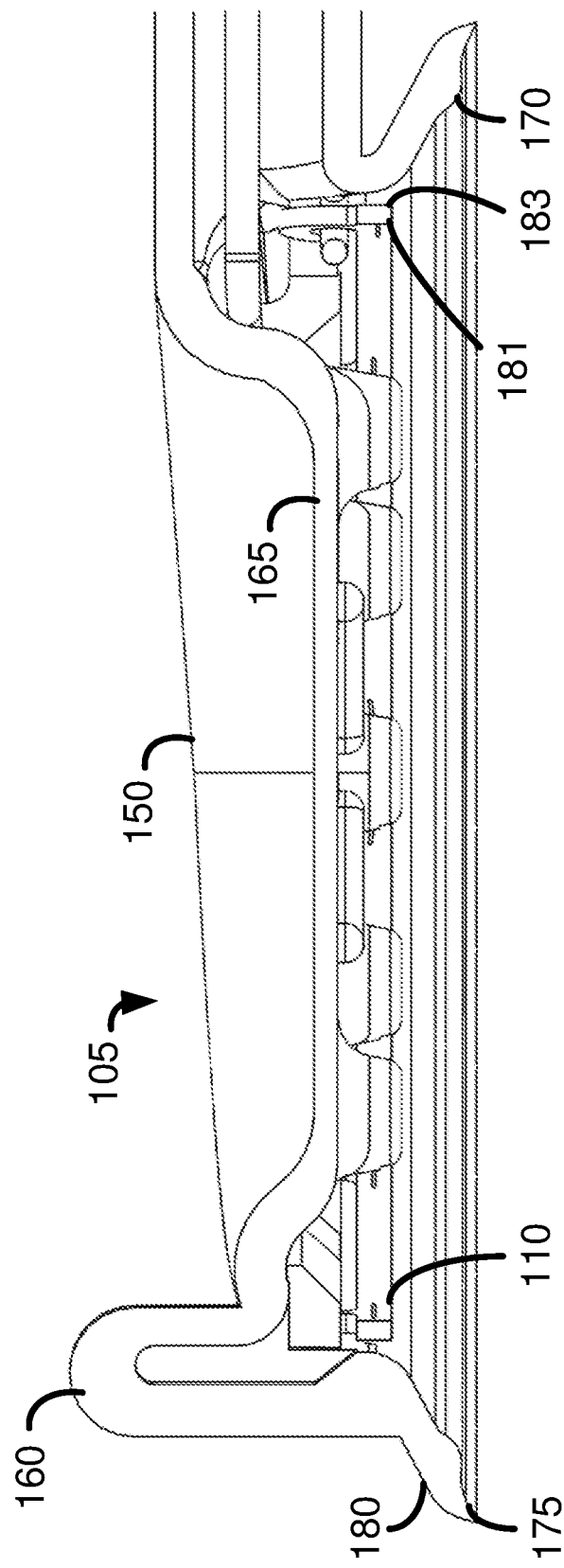
Figure 1D:
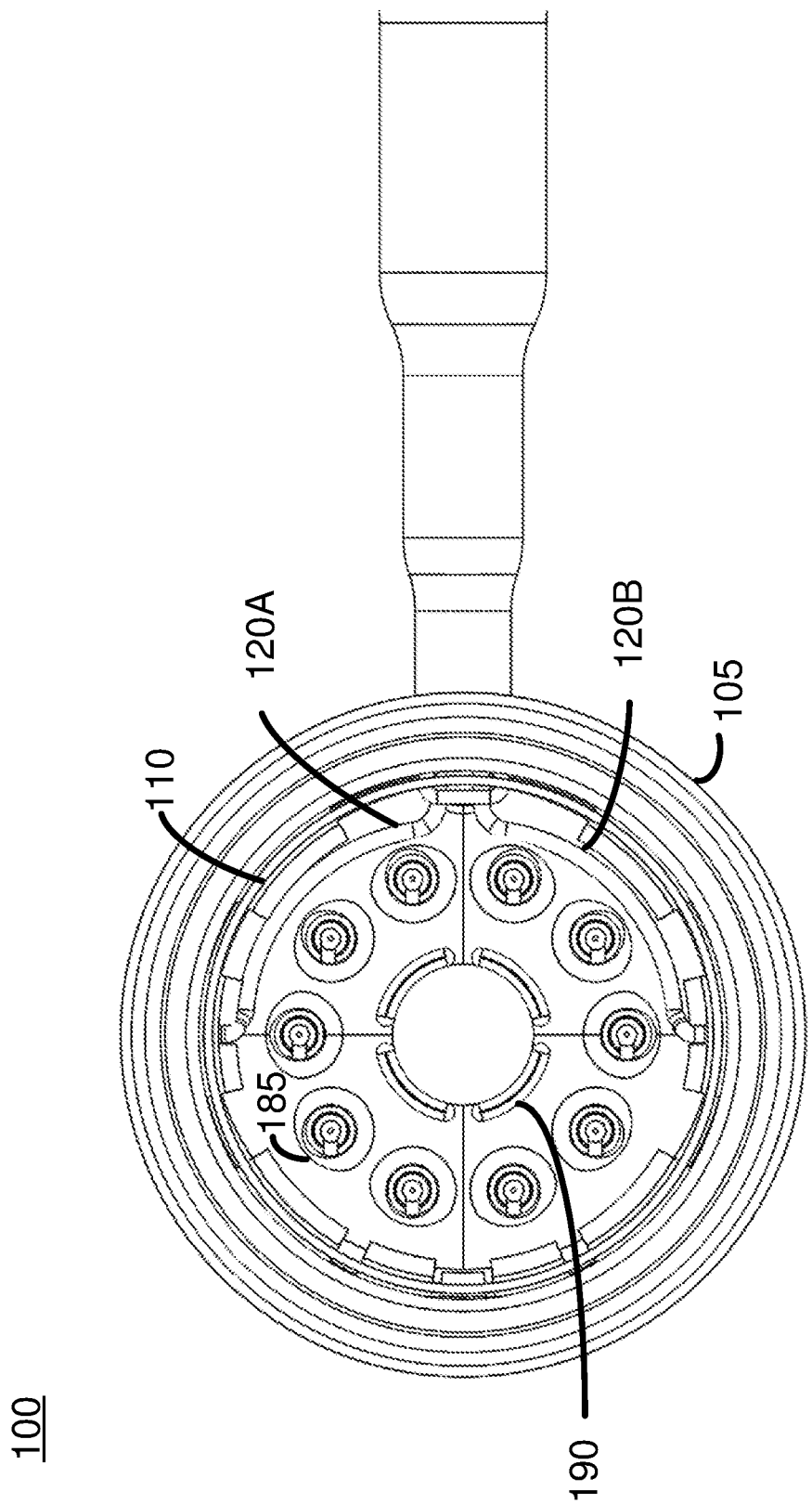
FIG. 1D illustrates a bottom view of the microsurgical device shown in FIG. 1A, according to one embodiment.
Figure 1E:
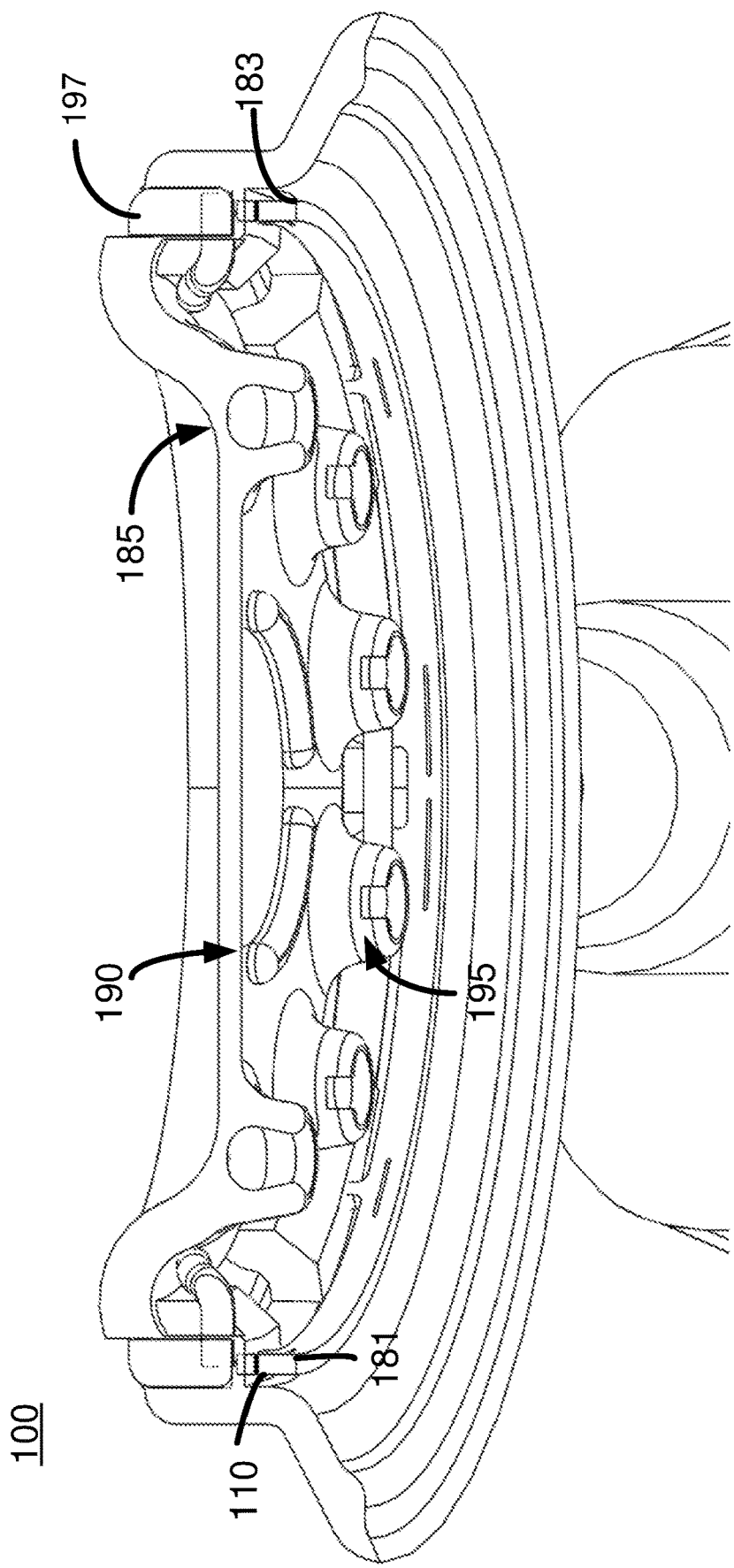
FIG. 1E illustrates a bottom perspective view of the microsurgical device shown in FIG. 1A, according to one embodiment.
Figure 1F:
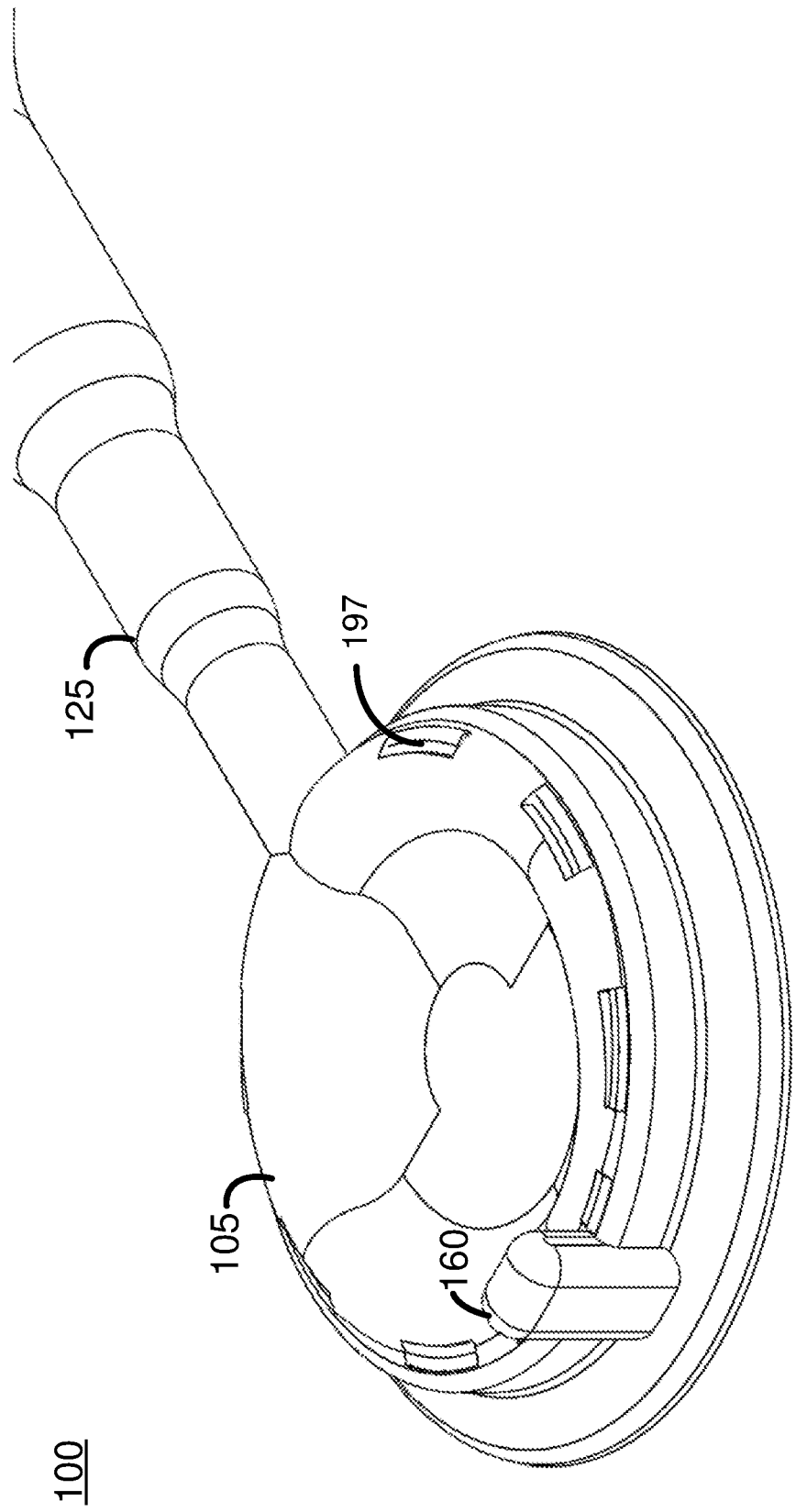
FIG. 1F illustrates a top perspective view of the microsurgical device shown in FIG. 1A, according to one embodiment.

Figures (FIGS. 1A-1F illustrate various views of a microsurgical device 100 for tissue cutting. FIG. 1A illustrates an embodiment of a microsurgical device 100. FIGS. 1B-1C illustrate cross-sectional views of the microsurgical device 100. FIG. 1D illustrates a bottom view of the microsurgical device 100. FIG. 1E illustrates a bottom perspective view of the microsurgical device 100. FIG. 1F illustrates a top perspective view of the microsurgical device 100.

The device 100 shown in FIG. 1A includes a suction cup 105, a cutting element 110 (also referred to as "cutting ring" herein), one or more suction tubes 115, electrical leads 120A, 120B, and a stem 125. The suction cup 105 and cutting element 110 are located at a distal end of the stem 125, which houses the one or more suction tubes 115 and the electrical leads 120A, 120B. The device 100 further includes a control console 130 (also referred to as "controller" herein) that is configured to provide suction to the suction cup 105 and electrical energy to the cutting element 110. The suction cup 105 is connected to the control console 130 via the one or more suction tubes 115 and a suction connector 135. The cutting element 110 is connected to the control console 130 via the electrical leads 120A, 120B, one or more sets of electrical conductors, such as electrical conductors 140A, 140B, and an electrical connector 145.

The suction cup 105 is a foldable structure that can provide a water-tight seal between the edges of the suction cup 105 and the tissue being excised (e.g., lens capsule, corneal tissue, connective tissue, and the like). Because of the fluidic seal between the suction cup 105 and the tissue, vacuum pressure can be applied to the suction cup 105 and the tissue so that the resulting pressure presses the cutting element 110 against the tissue. Pressing the cutting element 110 against the tissue facilitates a more precise, smoother cut. The foldable structure of the suction cup 105 is reversibly collapsible such that a cross-section of the suction cup 105 can decrease for insertion of the device 100 through an incision. As such, the suction cup 105 may include a compliant material, such as silicone, polyurethane, and the like. In one embodiment, the material of the suction cup 105 is a medical grade silicone having a Shore A durometer of 60 (e.g., Nusil MED-4960). Further, the silicone may be clear, which may assist in the placement of the suction cup 105.

The cutting element 110 is an element designed to cut tissue through application of pressure and/or electrical current via one or more electrical leads 120A, 120B coupled to the cutting element 110. The cutting element 110 can be made from various materials. In some embodiments, the metallic components of the cutting element 110 may be made by electroforming suitable materials such as nickel, nickel-titanium alloys, gold, steel, copper, platinum, iridium, molybdenum, tantalum, and the like. When the cutting element 110 is configured to electrically excise tissue, the material for the cutting element 110 is electrically conductive. In addition, the cutting element 110 is reversibly collapsible such that a cross-section of the cutting element 110 can decrease for insertion of the device 100 through an incision. Therefore, the material of the cutting element 110 is generally elastic so that it can return to its original shape after insertion of the device 100 through the incision. A typical construction example is a superelastic nitinol ring having a wall thickness of 0.075 mm, height of 0.140 mm, and tabs. Another strategy is to add to this superelastic body a thin film (e.g., 0.0001 to 0.002 mm) of a more conductive material that does not have to be superelastic because it is very thin. Examples of materials include, but are not limited to, spring steel, stainless steel, titanium nickel alloy, graphite, nitinol, nickel, nickel-chrome alloy, tungsten, molybdenum, tantalum, gold, silver, or any other material that will allow the cutting element 110 to return to its prior shape.

The device 100 is capable of delivering a wide range of energies (e.g., from 0 to 3 joules, or more) via the cutting element 110. The energy dissipated by the cutting element 110 during use in surgery may be determined empirically through use on a specific tissue of interest. For example, in a capsulotomy of the anterior lens capsule of an adult human, it was found that about 1.2 joules produced a satisfactory result. Some specific example of applications to lens capsulotomies include pediatric as well as adult humans and other animals such as dogs, listed in order of increasing energy need. To accommodate the varying energy needs, the amount of energy dissipated by the cutting element 110 may be controlled by controlling parameters such as the number of pulses, duration of each pulse, time between pulses, and/or energy of each pulse applied to the tissue via the cutting element 110. These parameters may be determined empirically for each tissue application and/or via computational modeling. In addition, temperature gradients in the cutting element 110 may be designed and/or modified for different tissues.

The one or more suction tubes 115 are located within the stem 125 of the device 100. The one or more suction tubes 115 are configured to provide suction to the suction cup 105. The one or more suction tubes 115 provide suction to the suction cup 105 to compress the suction cup 105 against the tissue being excised. The one or more suction tubes 115 may also be configured to reverse the suction and/or fluid flow being applied to the suction cup 105 to disengage the suction cup 105 and cutting element 110 from the excised tissue. In some embodiments, the material of the suction tubes 115 is a medical grade silicone having a Shore A durometer of 60 (e.g., Nusil MED-4960). In some embodiments, the electrical leads 120A, 120B, an anchor thread, and/or a rigid extender run through the one or more suction tubes 115 to the suction cup 105.

The one or more suction tubes 115 may be further configured to act as fluid paths. For example, the one or more suction tubes 115 may be primed before use with a solution, such as a balanced salt solution. Priming the fluid paths of the one or more suction tubes 115 may help ensure that there is little to no compressible air in the device 100. In addition, after excision of the tissue is complete, a hydraulic release of the one or more suction tubes 115 may be performed to release the suction cup 105 from the tissue. In some embodiments, the hydraulic release consists of forcing 0.05 ml to 0.2 ml of a balanced salt solution from the suction tubes 115 back into the suction cup 105.

The configuration of the one or more suction tubes 115 along the inner surface of the suction cup 105 may vary. For example, when there are two or more suction tubes 115, the suction tubes 115 may be located at antipodal points of the suction cup 105. This configuration may ensure equal distribution of suction throughout the suction channels of the suction cup 105. In other embodiments, the suction tubes 115 may be adjacent, located within a threshold number of degrees of each other, located within a threshold distance of each other, and the like. Further, the suction tubes 115 may be located along an outer surface of the suction cup 105, along a bottom surface of the suction cup 105, along a top surface of the suction cup 105, and the like. In embodiments where the device 100 includes a single suction tube 115, the suction tube may be located at any point along the inner surface of the suction cup 105. For example, an orifice of the suction tube 115 may be located in a roof of the suction cup 105, at a proximal end of the suction cup 105, at a distal end of the suction cup 105, and the like.

The electrical leads 120A, 120B are configured to provide electrical energy to the cutting element 110. The electrical leads 120A, 120B are located within the stem 125 of the device 100 and coupled to a surface of the cutting element 110. In some embodiments, the electrical leads 120A, 120B are silver wires. In other embodiments, the electrical leads 120A, 120B are made of copper, aluminum, gold, or the like. In addition, the electrical leads 120A, 120B may insulated.

The control console 130 is configured to provide suction to the suction cup 105 and electrical energy to the cutting element 110. In addition, an operator of the device 100 may control the depth of cut via the control console 130 by modifying the suction and/or electrical parameters of the device 100.

Suction is provided to the suction cup 105 via one or more suction tubes 115 connected to the control console 130 and a suction connector 135. Using the control console 130, an operator of the device 100 may provide suction to the suction cup 105, reverse suction during disengagement of the device 100, and/or flush the fluid paths of the one or more suction tubes 115 with a solution. In addition, an operator of the device 100 may modify the amount of suction applied to the suction cup 105 based on the operation being performed. In some embodiments, an operator of the device 100 may manually modify the amount of suction applied to the suction cup 105, for example using a vacuum valve and/or a vacuum gauge of the control console 130. Alternatively, or additionally, the control console 130 may include predetermined suction parameters determined via experimentation, modeling, and/or a combination thereof that are each associated with a procedure. In addition, using the control console 130, different amounts of suction may be provided to different suction tubes. By way of example, suction pressure of 19 +/−1 inch of Hg vacuum has been used successfully. That is gauge pressure, not absolute pressure, so the same pressure differential is established by the control console 130 across the suction cup wall regardless of altitude at which it is used.

The control console 130 delivers electrical energy to the cutting element 110 via the electrical leads 120A, 120B, one or more sets of electrical conductors 140A, 140B, and an electrical connector 145. A first set of electrical conductors 140A may be configured to provide power to the cutting element 110. A second set of electrical conductors 140B may be for resistance measurement and may be connected to a measurement device, such as a Kelvin probe (also known as the 4-wire resistance measurement method). In some embodiments, the first set of electrical conductors 140A and/or the second set of electrical conductors 140B are copper wires, such as (respectively) 24 ga copper wires, 30 ga copper wires, and the like. In other embodiments, the first set of electrical conductors 140A and/or the second set of electrical conductors 140B are composed of aluminum, gold, silver, or the like. Electrical energy may be provided to the cutting element 110 as one or more electrical waveforms. The one or more electrical waveforms are discharged through the cutting element 110 to cause the cutting element 110 to heat up for a short time, such as 0.0001 seconds to 0.05 seconds, depending on the applied voltage and current.

Using the control console 130, the depth of cut may be controlled by controlling the amount of electrical discharge applied to the cutting element 110. For example, the depth of cut may be controlled by modifying one or more of: the energy of each pulse, the number of pulses in the pulse train, the inter-pulse intervals, and the like. As with the suction, these parameters may be manually modified by an operator of the device 100 using control elements of the control console 130. Alternatively, or additionally, the control console 130 may include predetermined sets of parameters that are each associated with different depths of cut, different patient types, and the like. These sets of parameters may be determined through experimentation, modeling, and/or a combination thereof. The control console 130 may be a controller, microprocessor, a programmable hardware logic, etc.

In some embodiments, the control console 130 may change the operating parameters of the device 100 automatically. For example, the control console 130 may change the operating parameters according to a predetermined set of operating steps associated with a procedure. Alternatively, or additionally, the control console 130 may change the operating parameters of the device 100 based on feedback from the device 100 itself. For example, the control console 130 may change the operating parameters of the device 100 in response to a detection of a device resistance, a pressure, a pressure change, a temperature, a temperature change, a determined depth of cut, or the like, during use.

FIG. 1B illustrates a cross-sectional view of the device 100. In the embodiment shown, a height of the proximal end of the suction cup 105 is greater than a height of a distal end of the suction cup 105, forming a tapered circumferential suction chamber 150 in the suction cup 105. The tapered circumferential suction chamber 150 helps ensure even suction is applied, in part, because the height of the chamber decreases as the volume to be evacuated reduces.

In some embodiments, a first height of the tapered circumferential suction chamber 150 may have a first height at an orifice of the suction cup 105 and a second height at an antipodal point of the suction cup. In these embodiments, the first height may be larger than the second height. For example, the height of the suction cup 105 may be greatest at the proximal end and shortest at the distal end. In some embodiments, the relative heights of the proximal end of the suction cup 105 and the distal end of the suction cup 105 may be based on a number of factors, including, but not limited to: the amount of total volume to be evacuated, the amount of suction being applied, the type of procedure being performed, the type of tissue being excised, the amount of electrical energy being applied, features included on the underside of the suction cup 105 (e.g., standoffs and/or visual guides), or the like. For example, the tapered circumferential suction chamber 150 may slope at an angle so that the volume to be removed from the suction cup is proportional to the volume of the tapered circumferential suction chamber 150 along a horizontal axis of the suction cup 105. Examples of the slope angle include, but are not limited, 0 degrees, 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, or 15 degrees.

Figure 3A:
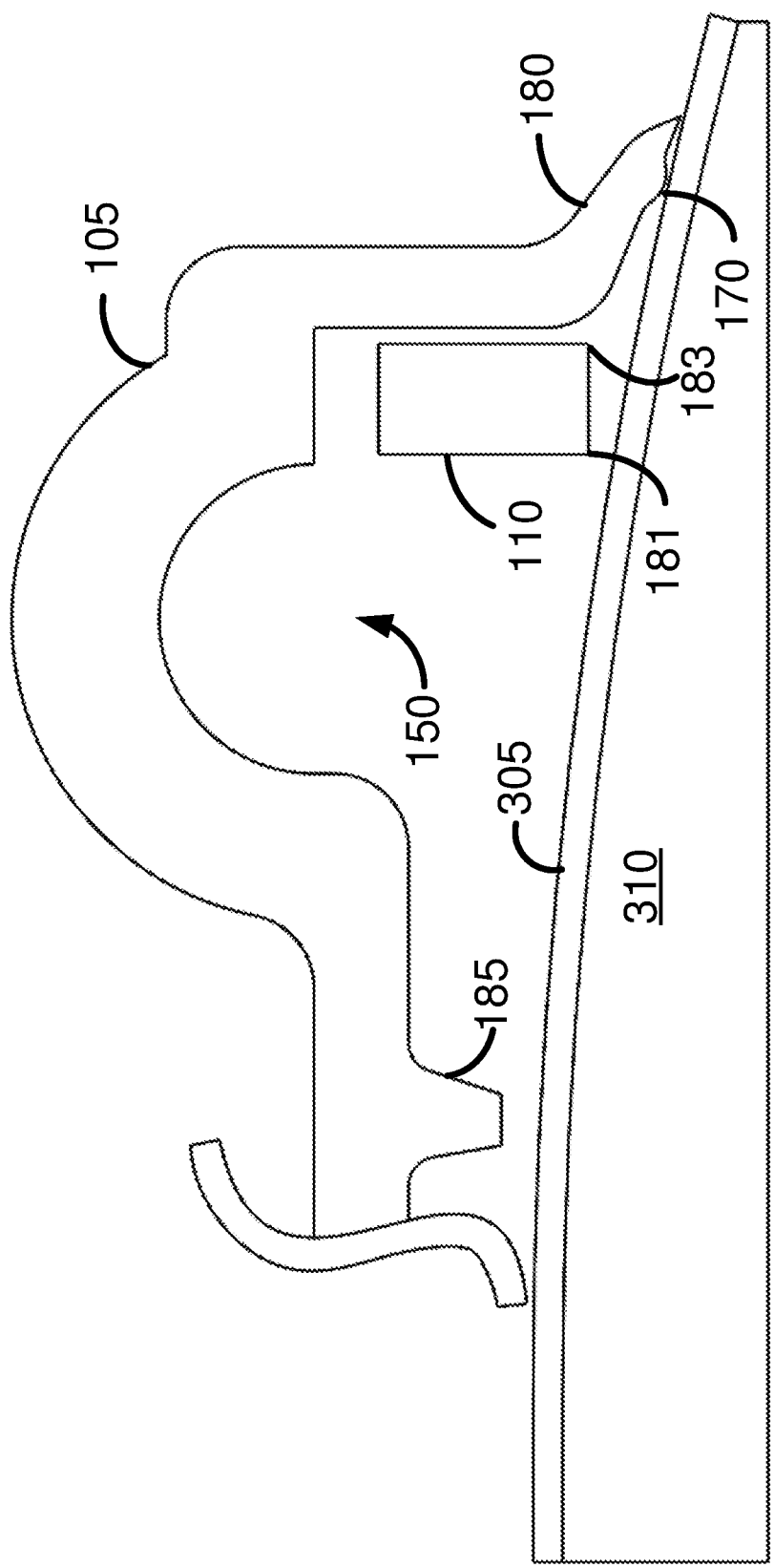
FIG. 3A-3F illustrate steps for using the device shown in FIG. 1A, according to one embodiment.

In addition, the geometry and specifications of the suction cup 105 may be modified to prevent collapse of the suction cup 105 when suction is applied. For example, the top of the tapered circumferential suction chamber 150 may be arched to prevent collapse, as shown in FIG. 3A. The rise and span of the arched portion may vary based on factors including, but not limited to the amount of suction being applied, the type of procedure being performed, or the like.

In addition, the thickness of the suction cup 105 may be modified to prevent collapse when suction is applied. In some embodiments, the thickness of the entire suction cup 105 is a uniform thickness that prevents collapse of the entirety of the suction cup (e.g., 200 microns or more, 175 microns or more, 150 microns or more, 125 microns or more, 100 microns or more, 75 microns or more, 25 microns or more, etc.). In other embodiments, portions of the suction cup may have various thicknesses. For example, portions that should not collapse during use, such as an arched portion of the suction cup 105, may be relatively thicker than other portions of the suction cup 105 that are collapsible during use. In these embodiments, the portions that have an increased thickness may have a thickness around 200 microns or more. Other portions of the suction cup may have thicknesses around 200 microns or less, such as 175 microns or less, 150 microns or less, 125 microns or less, 100 microns or less, as 75 microns or less, 50 microns or less, 25 microns or less, or the like. By limiting the portions of the suction cup 105 that have increased thicknesses, the total amount of silicon required to manufacture the suction cup 105 is reduced and collapse of the suction cup 105 is prevented. Further, by reducing the amount of silicon, the force needed to insert the suction cup 105 through an incision is reduced.

The stem 125 is coupled to the proximal end of the suction cup 105 via an opening within a tapered side of the suction cup 105. A neck 155 of the stem 125 enables the flow of fluid to and from the stem 125 into the suction cup 105 in a direction substantially perpendicular to the direction of the suction force being applied against the tissue. For example, the angle between the flow of fluid to and from the stem 125 and the direction of the suction force being applied against the tissue may be between 85 degrees and 95 degrees, between 80 degrees and 100 degrees, and the like. The substantially perpendicular flow helps ensure uniform distribution of suction. In alternative embodiments, the neck 155 of the stem 125 may be configured to provide substantially vertical flow. In these embodiments, an additional mechanism may be coupled to the neck 155 of the stem 125 to facilitate horizontal flow of suction and/or fluid to the suction cup 105 from the stem 125.

As previously discussed, the device 100 may include a rigid extender (not shown) that is used to extend the cutting element 110 for insertion of the device 100 through an incision, such as a corneal incision. The end of the rigid extender may include one or more prongs to which the cutting element 110 is coupled. The one or more prongs may prevent substantial decoupling of the rigid extender and cutting element 110 during transport. However, the length of the one or more prongs may necessitate a containment pocket 160 that prevents the one or more prongs from puncturing the suction cup 105.

A basic principle of injection molding in device manufacturing is that the intended molded part must not have features that create significant undercuts and prevent the separation of the two mold halves and retrieval of the molded part. In certain cases, the use of side pins may create the desired molded features but involve greater cost and may impart less precision. A horizontal containment pocket may represent a significant undercut and may not be able to be manufactured using standard molding techniques with two mold halves that separate in a vertical direction.

To remove the presence of an undercut created by a horizontal containment pocket, the containment pocket 160 may be collapsible between a vertical position and a horizontal position. In some embodiments, the containment pocket 160 may be collapsible between horizontal and vertical positions because of the flexibility of the material of the containment pocket 160. In alternative embodiments, the containment pocket 160 may be collapsible because of one or more joints, or any other suitable collapsing mechanism. For ease of manufacturing, the containment pocket 160 may be molded in the vertical position. The vertical position of the containment pocket 160 helps ensure the containment pocket is easily released as the two mold halves are pulled in a vertical direction to separate. When the containment pocket 160 is collapsed into the horizontal position, it can accept the end of the rigid extender. In some embodiments, the containment pocket 160 is constrained to lie horizontally during transport. It may remain horizontal as the suction cup 105 and cutting element 110 are elongated via a rigid extender. As the rigid extender is retracted, the containment pocket 160 returns to its vertical as molded shape due to silicone's elasticity.

FIG. 1C illustrates an additional cross-sectional view of the device 100. As discussed with reference to FIG. 1B, the suction cup 105 may form a tapered circumferential suction chamber 150 that slopes downward in a direction from the proximal end to the distal end of the suction cup 105. In addition, a central portion 165 of the suction cup 105 may have a shorter height than the tapered circumferential suction chamber 150 of the suction cup 105. The shortened height of the central portion 165 may reduce the amount of material needs to be evacuated from within the space enclosed by the suction cup 105, which facilitates a more uniform distribution of suction. In some embodiments, the entirety of the central portion 165 may be of uniform height. In alternative embodiments, the central portion 165 may slope at the same angle as the tapered circumferential suction chamber 150 or at a different angle as the tapered circumferential suction chamber 150. In addition, the height (s) of the central portion 165 may vary based on the amount of total volume to be evacuated, the amount of suction being applied, the type of procedure being performed, the type of tissue being excised, the amount of electrical energy being applied, features included on the underside of the suction cup 105 (e.g., standoffs and/or visual guides), or the like.

As illustrated in FIG. 1C, the suction cup 105 includes a sealing contact 170 and a tapered edge 175 along the skirt 180 of the suction cup 105. The compliant skirt 180 enables the sealing contact 170 to remain on the capsular membrane even if a handpiece of the device 100 is rotated or translated by an operator of the device 100. The tapered edge 175 may facilitate the placement of the compliant skirt 180 under the iris, e.g., for procedures involving small pupils. In some embodiments, the tapered edge 175 is where a mold parting line is located. The distance between the tapered edge 175 and the sealing contact 170 may be such that flash from the molding process is not long enough to reach the sealing contact 170. For example, a flash) up to 0.25 mm long will not get between the seal and the capsule and cause a leak.

As further illustrated in FIG. 1C, the proximity of the cutting element 110 to the suction cup 105 may help ensure that only inner bottom edge 181 of the cutting element 110 is in physical contract with the tissue being excised (e.g., a capsular membrane). For example, the cutting element may be coupled to a surface of the suction cup such only the inner bottom edge 181 of the cutting element is in contact with the tissue being excised. In these embodiments, upon application of suction to the suction cup 105, the outer diameter of the cutting element 110 is not in physical contact with the tissue being excised. In these embodiments, the outer diameter of the cutting element 110 affects tissue excision remotely through conduction. For example, the outer diameter of the cutting element 110 may be located at a sufficient distance from the capsular membrane to remotely affect the capsular membrane by a temperature change. The temperature change may assist in the creation of a consistent rolled edge, discussed below with reference to FIGS. 3A-3F. In other embodiments, the coupling of the cutting element 110 and suction cup 105 may be configured such that the outer bottom edge 183 of the cutting element excises the tissue, both the inner bottom edge 181 and outer bottom edge 183 excise the tissue, or any other suitable portion of the cutting element 110 excises the tissue.

FIGS. 1D-1F illustrate additional views of the device 100. As shown in FIG. 1D, the cutting element 110 and electrical leads 120A, 120B are installed. In some embodiments, the electrical leads are electrically insulated silver wires (e.g., 6-micron thick layer of polyimide). In some embodiments, the electrical leads 120A, 120B are pushed back near the top of the interior flow chamber to be out of the way of the cutting edge (e.g., the inner bottom edge 181) of the cutting element 110.

The suction cup 105 shown includes one or more features. Features shown may include hollow standoffs, such as hollow standoff 185, and aiming guides, such as aiming guide 190. In the embodiment shown, the hollow standoffs are placed on an inner surface of the suction cup 105. The hollow standoffs prevent the central portion 165 of the suction cup 105 from completely sealing against the capsular membrane surface, creating channels for material flow and a uniform distribution of suction. In addition, the hollow standoffs may provide a visual indication of the suction level within the suction cup 105. As suction develops, the trapped air bubble is removed from the inside of the hollow standoff. The escape of the air bubble can be used as a visual signal that adequate suction has been developed. The dimensions of the standoffs and aiming guides be varied to select one that traps air bubbles and allows escape only when the desired level of suction has been applied. In some embodiments, the dimensions of the standoffs may vary such that they provide a visual indication of different levels of suction.

In the embodiment shown, the suction cup 105 includes ten stand-offs. In alternative embodiments, the suction cup 105 may include any suitable number of standoffs, such as one standoff, five standoffs, or the like. In some embodiments, the standoffs have a high aspect ratio air traps (e.g., 0.2 mm diameter and 0.3 mm height). In alternative embodiments, the standoffs have low aspect ratio air traps, intermediate aspect ratio air traps, and the like. Further, the aspect ratio can be modified to ensure that air is always trapped. Because silicone rubber is stretchable, the standoff opening can have a smaller diameter than the trap cavity and still be moldable. Reduced diameter at the opening of the standoff may help ensure that air will be trapped until suction reaches the pressure needed for a successful capsulotomy. However, the diameter of the cavity may include smaller and/or equal dimensions as the standoff opening.

In some embodiments, the standoffs include a slot, e.g., slot 195. The slots face away from the stem 125 and/or suction tubes 115. In alternative embodiments, the slots may face the stem and/or suction tubes 115, each slot may face a different direction, or the like. The slots may be modified to let air out at different levels of suction.

The placement of the capsulotomy at a precise location on the surface of the lens is critical as off-centered capsulotomies may provide less IOL stability and poorer IOL optical performance. The surgeon may use a number of different surgical landmarks to center the capsulotomy. These include the positions of certain Purkinje images or light reflections that may be used to indicate the position of the patient's visual axis. An automated capsulotomy device, such as device 100 should allow easy centration of the cutting element 110 aligned with such Purkinje images. In the device 100 shown, the alignment of the center of the suction cup 105 with a desired surgical landmark such as a Purkinje light reflection is assisted by the placement of aiming guides, such aiming guide 190, near the center of the suction cup 105. Aiming guides may have various geometric shapes and assist in the surgeon's visual recognition of the location of the center of the suction cup 105 and/or the cutting element 110. Aiming guides may be manufactured onto the suction cup 105 using silicone micro-molding techniques that are well known in the art.

Once the desired alignment of the suction cup 105 has been identified, the initiation of suction must not cause a substantial shift in the position of the cutting element 110, which may result in an off-centered capsulotomy. Undesirable movement of the cutting element 110 can occur if the cutting element 110 is merely inserted into holes in the suction cup 105 that do not completely constrain cutting element 110 movements as the suction cup 105 reduces its internal volume under suction. To prevent undesirable movement, the cutting element 110 may be physically bonded to the suction cup 105, as shown in FIG. 1E.

The cutting element 110 consists of a conductive metal and the suction cup 105 may consist of silicone and thus are made as two separate parts. Hollow pockets, such as pocket 197 are disposed in the suction cup 105 to accept one or more tabs protruding from the cutting element 110. During manufacture, the tabs are placed within the corresponding hollow pockets and silicone is deposited into the hollow pockets to secure the attachment tabs in place. In some embodiments, the silicone is potted from the topside of the suction cup 105. In alternative embodiments, the silicone is potted from the bottom side of the suction cup 105. For example, during bottom potting, liquid silicone may be dispensed in each pocket. The cutting element 110 is then brought to the suction cup 105, the electrical leads 120A, 120B are fed through the lumen of the stem 125, and the attachment tabs are submerged in the liquid silicone in the potting pockets. The assembly may then be heated to cure the silicone. In some embodiments, the pockets include a thin membrane that prevents the liquid silicone from getting onto the cutting element 110. The thin membrane may be pierced by the attachment tabs as the attachment tabs are placed into the hollow pockets.

Figure 2:
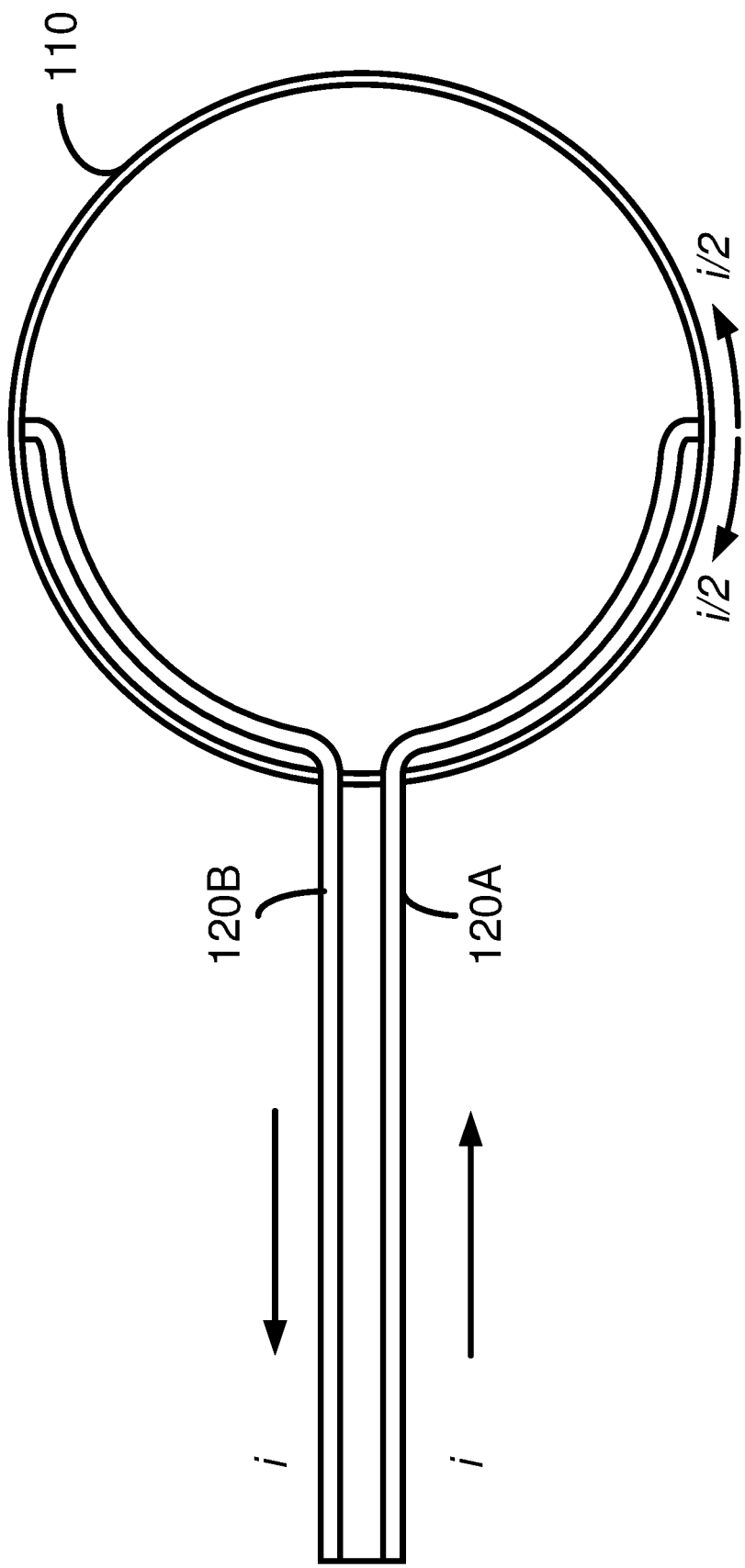
FIG. 2 illustrates the flow of current through the cutting element of the microsurgical device shown in FIG. 1A, according to one embodiment.

FIG. 2 illustrates the path of electrical current flow (i) within the cutting element 110. Upon entering the cutting element 110 through an electrical lead 120A, a portion of the current, such as one half of the current ($i_{1/2}$), travels along one half of the cutting element 110, while another portion of the current, such as the other half of the current ($i_{1/2}$), travels along the other half of the cutting element 110. Current then exits the cutting element 110 at the other electrical lead 120B. Due to the electrical resistance of the cutting element 110, the current flow causes a rapid increase in the temperature of the cutting element 110. Because of the rapid increase in temperature, the water molecules near or adjacent to the cutting element 110 and the tissue being excised vaporize rapidly and mechanically fracture the tissue along the path dictated by the portion of tissue being excised.

FIG. 3A-3F illustrate steps for using the device 100 shown in FIG. 1A, according to one embodiment. FIG. 3A a cross-section of the device 100 in close proximity to the capsular membrane 305 that encloses the lens capsule 310. In the cross-section shown, the suction cup 105 has a flow channel where the silicone is arched and thick enough to prevent collapse when the suction is applied, e.g., along tapered circumferential suction chamber 150 of the suction cup 105. The standoffs, such as standoff 185, keep the flow path under the center of the membrane open during suction. The body of the cutting element 110 illustrated has a rectangular cross-section. In alternative embodiments, the cutting element 110 may be any suitable shape, such as conical, elliptical, and the like.

The sealing contact 170 of the skirt 180 of the suction cup 105 comes into close proximity to the capsular membrane 305 which encloses the lens 310. An operator of the device centers the device 100 on the patient's visual axis. Once centered, the rigid extender has been retracted from its extended position such that the end of the rigid extender is in the neck 155 of the device 100. The rigidity of the rigid extender enables the surgeon to position the suction cup 105 on the visual axis over a large range of anterior chamber depth, ACD, (e.g., ACD 1.9 mm to 4.0 mm).

Figure 3B:
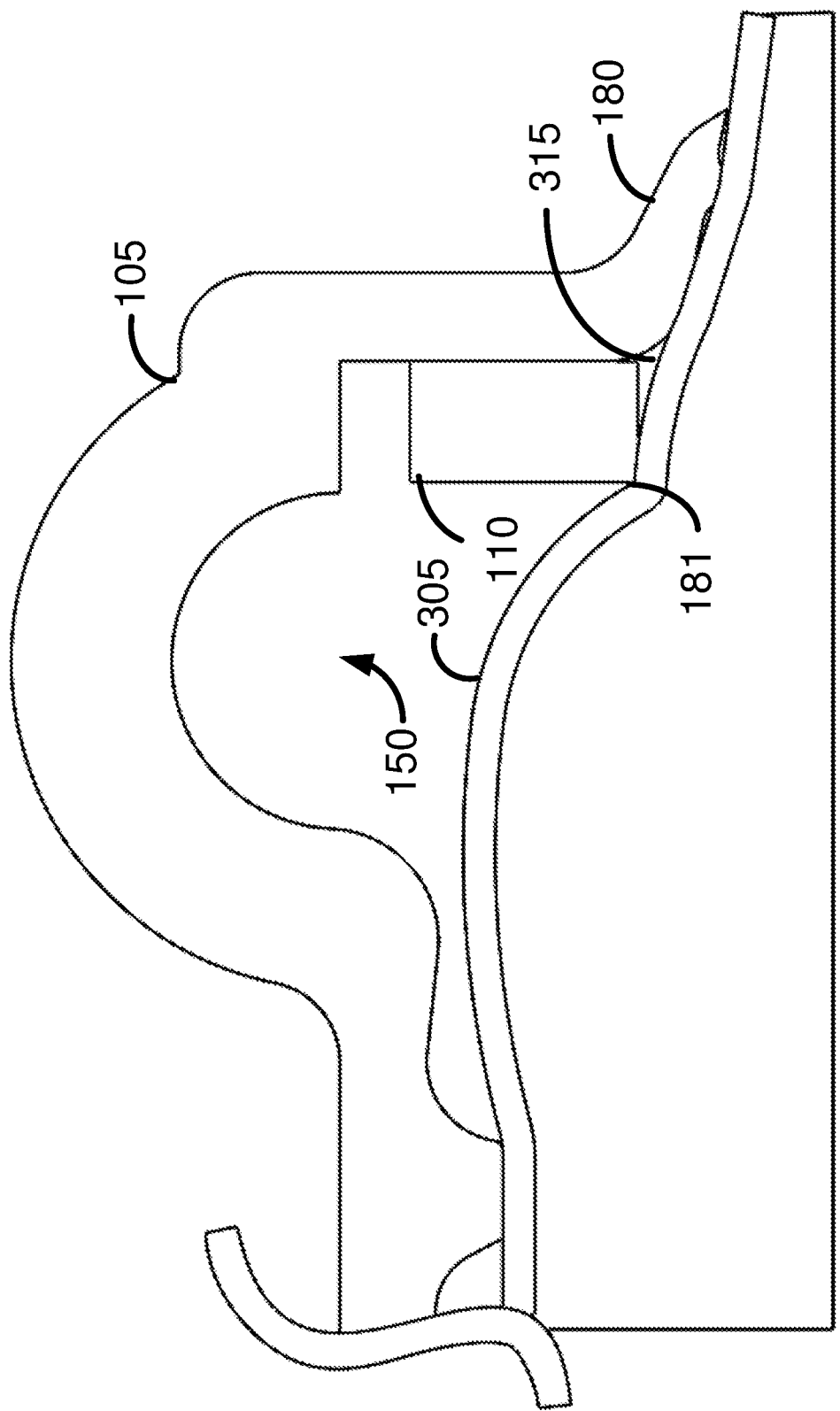

FIG. 3B illustrates the deformation of the lens 310 and suction cup 105 that occur when suction is applied to the suction cup 105. The suction forces pull the capsular membrane 305 inside the suction cup 105 and establish a contact force against the inner bottom edge 181 of the cutting element 110. Concurrently, a surface of the suction cup 105 is pulled against the outer surface of the cutting element 110. The skirt 180 of the suction cup 105 prevents contact between the capsular membrane and the outer bottom edge 183 of the cutting element 110 to limit cutting to the inner bottom edge 181 of the cutting element 110. In alternative embodiments, cutting may occur at the outer bottom edge 183 of the cutting element 110, at both the inner bottom edge 181 and outer bottom edge 183 of the cutting element 110, or the like.

A small volume 315 is created such that liquid there is trapped between the capsular membrane 305, cutting element 110, and suction cup 105. The stretching forces from suction causes capsular membrane 305 to develop significant tensile stress. There is a tensile stress concentration where the capsular membrane 305 is in contact with the inner bottom edge 181 of the cutting element 110. Since this tensile stress is built up prior to the electrical discharge that makes the cut, it is already there waiting to act at the instant that the discharge occurs, and a brief flash of heat is added. In some embodiments, small volume 315 separating the outer diameter of the cutting element 110 and the capsular membrane 305 is sufficiently small that it allows the cutting element 110 to remotely cause a temperature change in the capsular membrane 305 from a distance to aid in the capsular roll up after the cutting procedure is complete.

Figure 3C:
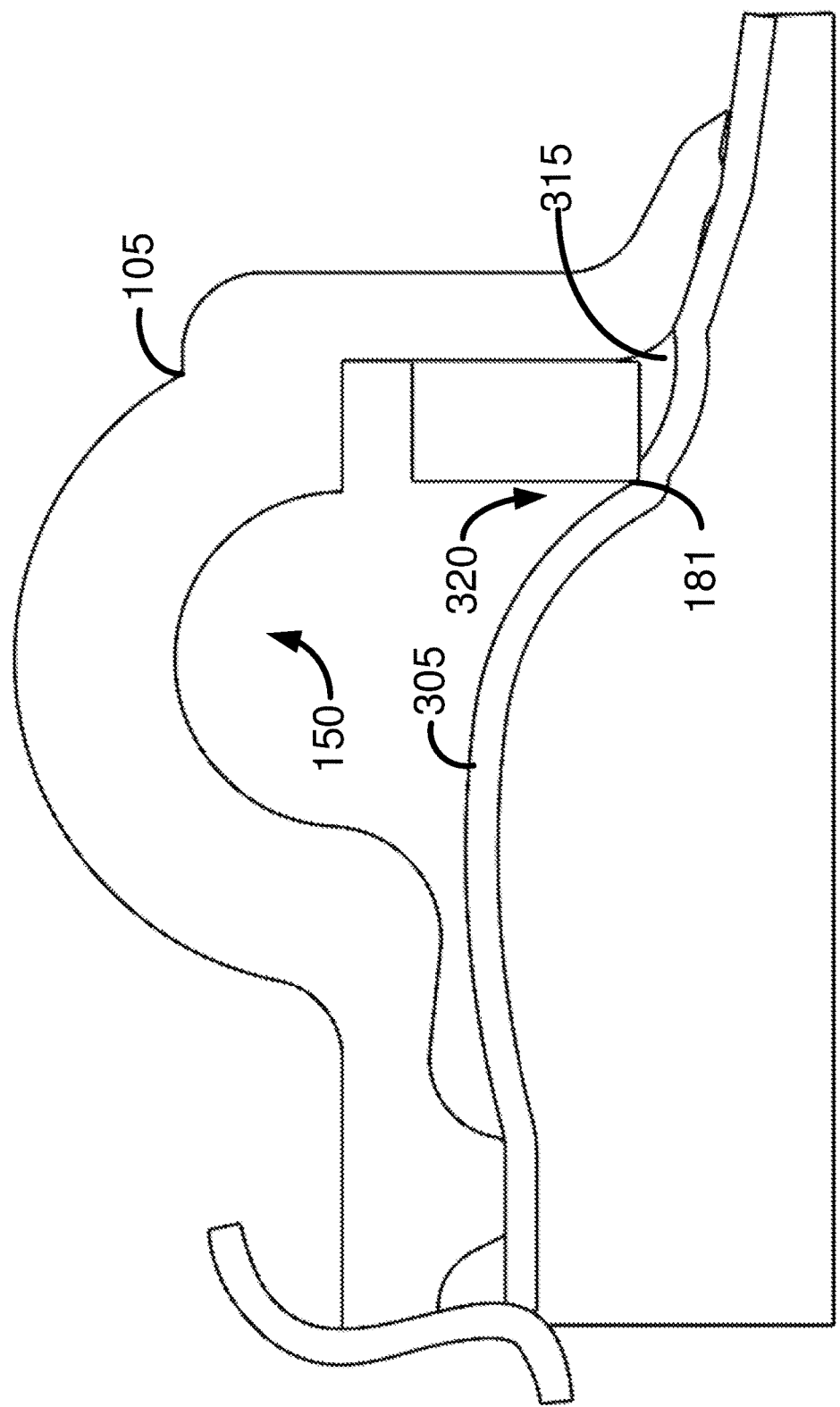

FIG. 3C illustrates the condition when the electrical discharge is occurring through the cutting element 110. Within the first few microseconds of the cutting event, the cutting element 110 heats up to a temperature hotter than the critical temperature of water. As a result, the water molecules located within a few microns of the cutting element 110 vaporize. The steam within the trapped small volume 315 cannot escape during this short time, so the pressure in the trapped small volume 315 rises. The increase in pressure results in the change of curvature that appears in the capsular membrane 305. This may also cause a change in volume of the small volume 315.

At the same time, heat is flowing from the cutting element 110 into the capsular membrane 305 at the point of contact with the cutting element 110 (e.g., the inner bottom edge 181 of the cutting element 110). As heat flows into the collagen at the point of contact between the capsular membrane 305 and the cutting element 110, the capsular membrane 305 weakens. Due to the symmetry of the device 100, equal forces and temperatures are exerted across the circumference of the cutting element 110 in contact with the capsular membrane 305. When the strength of the capsular membrane 305 is less than the forces acting to tear it, the capsular membrane 305 breaks. The forces acting to tear the capsular membrane 305 may arise from 1) the tensile stress from the suction being applied, and/or 2) the increasing pressure in the small volume 315 as a result of the steam heating up.

Because the cutting event, occurs on the millisecond time scale (e.g., 1 millisecond to 10 milliseconds), it is the inertia of the surrounding mass of material that confines the steam. It would take a great force to accelerate the surrounding mass of material during this brief time interval. During the millisecond time interval, the steam pressure builds, the material will start to move, but the capsulotomy is done by then. For example, the electrical discharge may consist of 12 pulses, 66 microseconds on, 305 microseconds off, for a total time of 4 milliseconds. This may not be enough time for the mass of material to accelerate and move. Note that the cutting of different thickness capsules or other tissues may be performed by altering the number of pulses, duration of each pulse, interpulse interval, and energy per pulse. In addition, the width of the bottom aspect of the cutting ring may be adjusted to change the spatial extent of remote temperature effects such as the roll up.

Figure 3D:
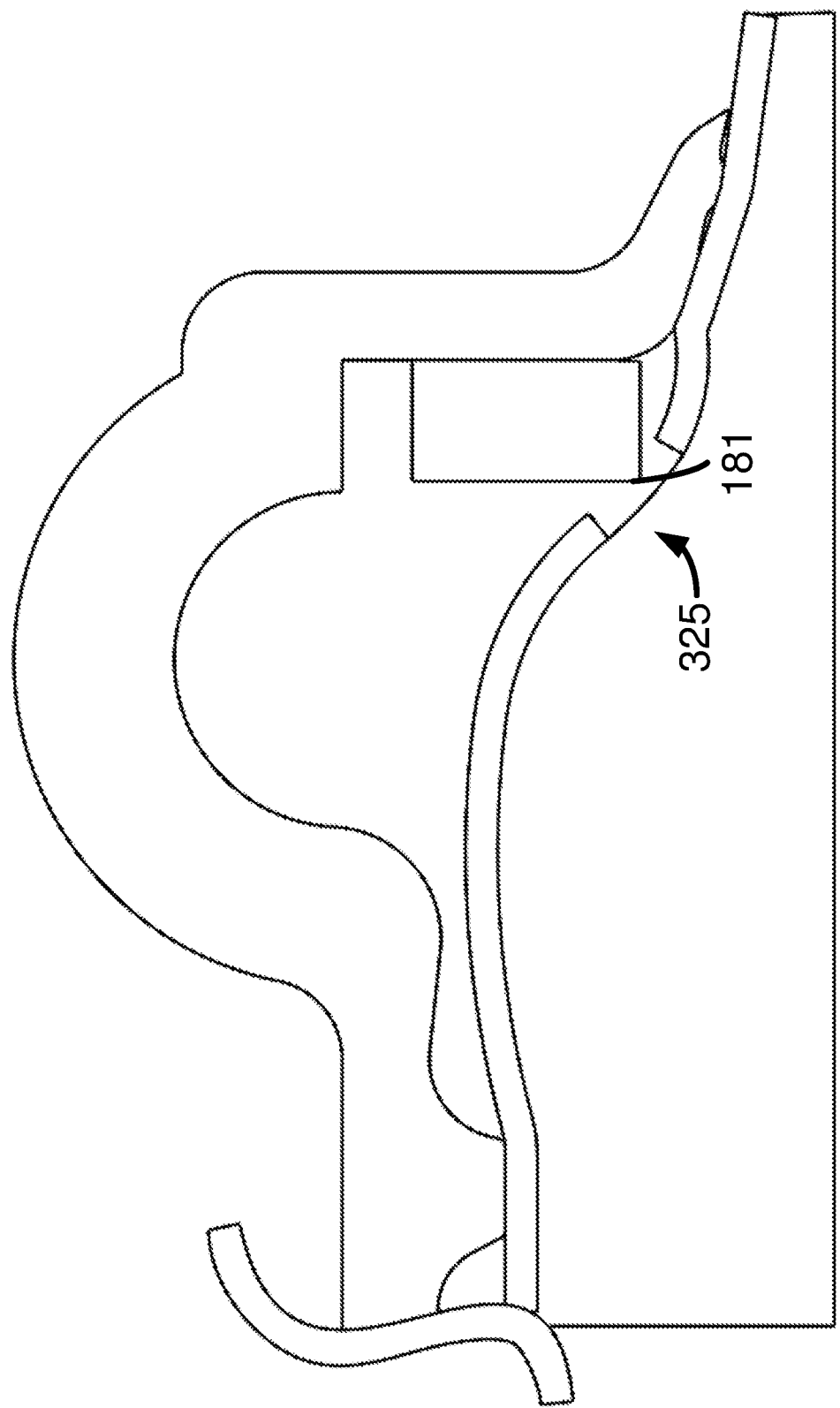

FIG. 3D illustrates the pullback 325 of the stretched capsular membrane 305 from the inner bottom edge 181 of the cutting element 110, which occurs after the electrical discharge has completed. In some embodiments, there is little inertial mass involved in this movement.

Figure 3E:
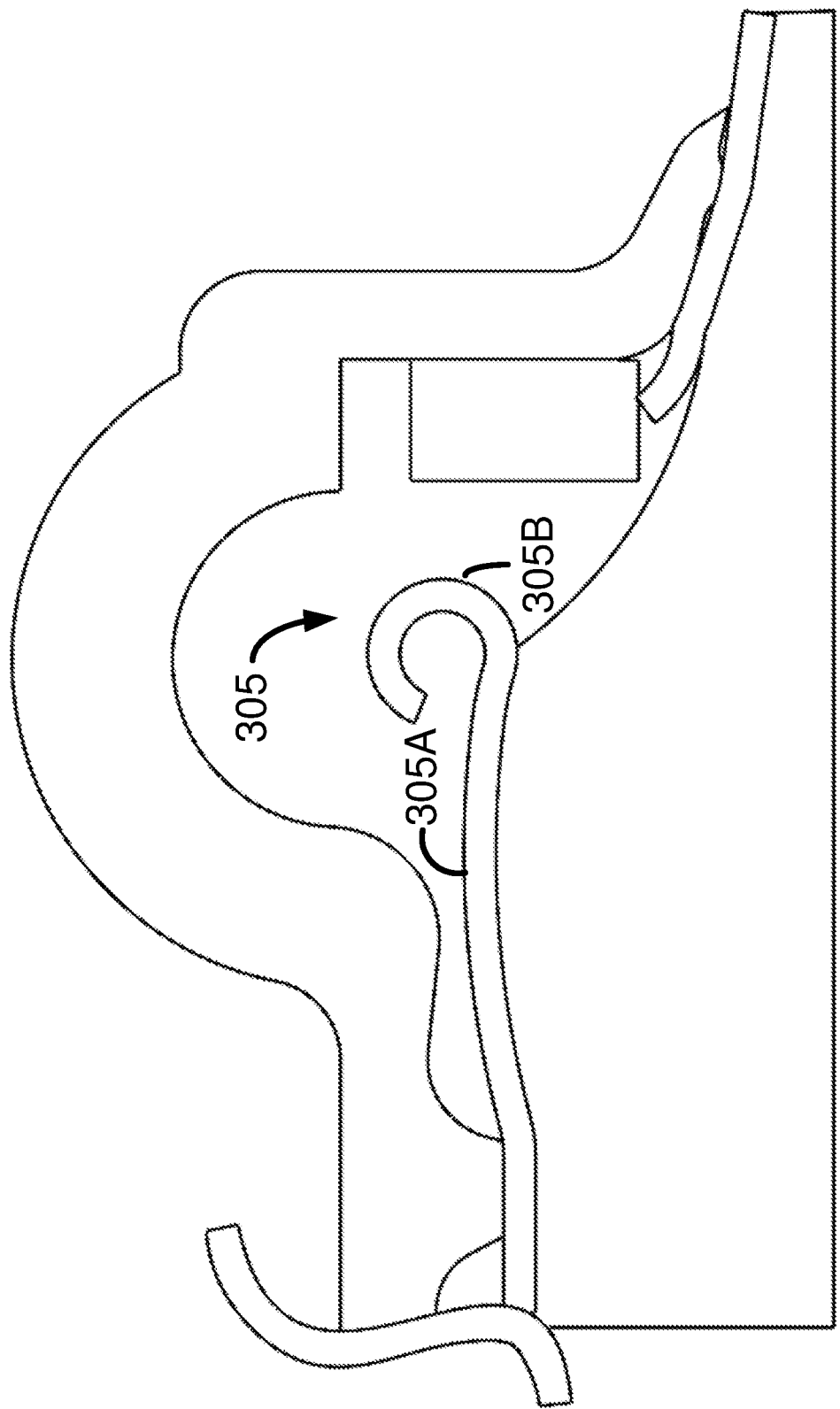

FIG. 3E illustrates the edges of the capsular membrane 305 roll up as edges cool. The edges of the capsular membrane 305 roll up because the heating method employed by the device 100 creates a temperature gradient through the thickness of the capsular membrane 305. As discussed with respect to FIG. 3B, the outer surface of the capsular membrane 305 will receive heat from the cutting element 110 through the steam that contacts it, such as the steam confined within the small volume 315. The heat causes the collagen to shrink. The collagen shrinks more at the outer surface 305A of the capsular membrane 305 than at the inner surface 305B of the capsular membrane 305 because the cutting event is too brief for significant heat to get through the steam layer and shrink the inner surface 305B of the capsular membrane 305 as much the outer surface 305A. This creates a tensile stress gradient through the thickness of the capsular membrane 305 as it cools down. The shrinkage of the collagen in the top layer pulls the edge in so it rolls up. The edge of the capsular bag can only roll up until it contacts the bottom of the cutting element 110 and/or the suction cup 105.

Figure 3F:
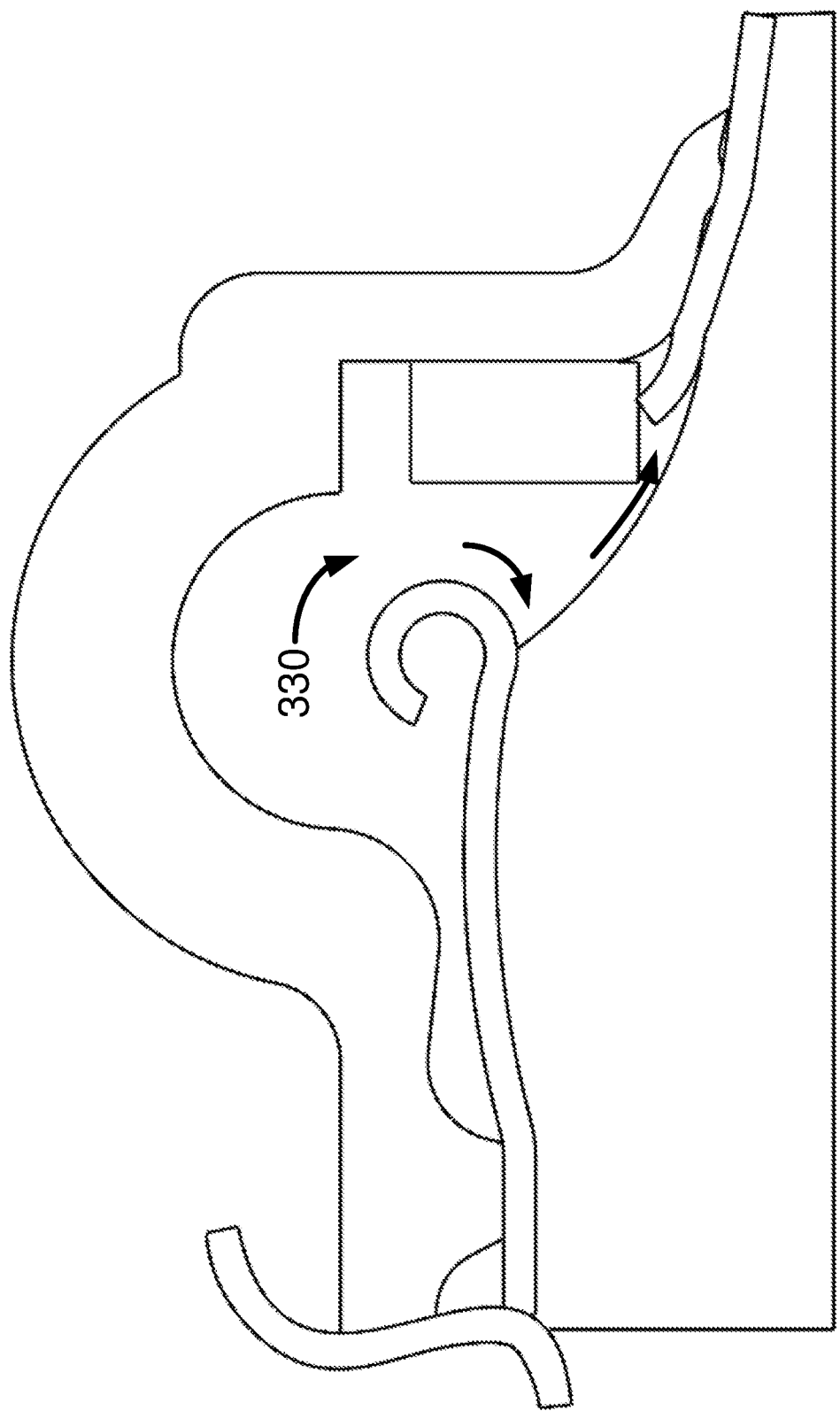

FIG. 3F illustrates the flow direction 330 of the fluid release that is performed to disengage suction and lift the suction cup 105 off the lens 310. Because the edge of the capsular bag is rolled up against the bottom of the cutting element 110 and suction cup 105, the flow at that location goes between the capsular membrane 305 and the lens 310. This performs a hydrodissection to separate capsular membrane 305 from the lens 310.

As the fluid release progresses, the edge of the capsular bag is still rolled up against the bottom of the suction cup 105, so fluid is still being directed between the capsular membrane 305 and the lens 310 to complete the hydrodissection. In some embodiments, the fluid release is performed rapidly (e.g., 0.5 seconds or less). If the release flow is fast enough, inertia of the surrounding fluid above the suction cup 105 may delay it rising long enough for the release flow to follow the path of the hydrodissection rather than simply floating off the suction cup 105. Once the edge of the capsule bag is no longer held down by the suction cup 105, the capsular bag is free to roll up under the influence of the surface stress induced by the flash of heat that came to it during the cutting event.

Additional Configuration Information

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims. As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

What is claimed is:

1. A device for excising tissue, the device comprising:
a suction cup forming a tapered suction chamber comprising a first taper that tapers from a perimeter of the suction chamber at a first height to a center of the suction chamber at a second height less than the first height, enabling a suction force to be applied against the tissue in a first direction, and wherein the suction cup comprises a second taper that tapers continuously from the first height at the perimeter of the suction cup at a proximal end of the suction cup around a circumference of the suction cup to a third height at a distal end of the suction cup, the third height less than the first height and greater than the second height;
a stem coupled to the proximal end of the suction cup via an opening within a tapered side of the suction cup such that a neck of the stem enables flow of fluid to and from the stem into the suction cup in a second direction substantially perpendicular to the first direction, wherein the neck of the suction cup has a first diameter and a proximal end of the stem has a second diameter, and wherein the second diameter is larger than the first diameter; and
a cutting element coupled to an inner surface of the suction cup and configured to excise the tissue.

2. The device of claim 1, wherein the suction cup has a tapered edge.

3. The device of claim 1, further comprising one or more tabs protruding from the cutting element, wherein one or more pockets of the suction cup are configured to receive the one or more tabs.

4. The device of claim 1, wherein the cutting element is coupled to the inner surface of the suction cup such that an inner bottom edge of the cutting element is configured to be in contact with the tissue being excised.

5. The device of claim 1, wherein a surface of the suction cup includes one or more aiming guides to provide an indication of an approximate center of the suction cup.

6. A device for excising tissue, the device comprising:
a suction cup forming a tapered suction chamber comprising a first taper that tapers from a perimeter of the suction chamber at a first height to a center of the suction chamber at a second height less than the first height, enabling a suction force to be applied against the tissue in a first direction, and wherein the suction cup comprises a second taper that tapers continuously from the first height at the perimeter of the suction cup at a proximal end of the suction cup around a circumference of the suction cup to a third height at a distal end of the suction cup, the third height less than the first height and greater than the second height;
a stem coupled to the proximal end of the suction cup via an opening within a tapered side of the suction cup such that a neck of the stem enables flow of fluid to and from the stem into the suction cup in a second direction substantially perpendicular to the first direction; and
a cutting element coupled to a surface of the suction cup and configured to excise the tissue.

7. The device of claim 6, wherein the suction cup has a tapered edge.

8. The device of claim 6, further comprising one or more tabs protruding from the cutting element, wherein one or more pockets of the suction cup are configured to receive the one or more tabs.

9. The device of claim 6, wherein a first portion of the stem has a first diameter and a second portion of the stem has a second diameter, and wherein the second diameter is larger than the first diameter.

10. The device of claim 6, wherein a surface of the suction cup includes one or more aiming guides to provide an indication of an approximate center of the suction cup.

11. A device for excising tissue, the device comprising:
a suction cup forming a tapered suction chamber comprising a first taper that tapers from a perimeter of the suction chamber at a first height to a center of the suction chamber at a second height less than the first height, enabling a suction force to be applied against the tissue in a first direction, and wherein the suction cup comprises a second taper that tapers continuously from the first height at the perimeter of the suction cup at a proximal end of the suction cup around a circumference of the suction cup to a third height at a distal end of the suction cup, the third height less than the first height and greater than the second height; and
a stem coupled to the proximal end of the suction cup via an opening within a tapered side of the suction cup such that a neck of the stem enables fluid flow to and from the stem into the suction cup in a second direction substantially perpendicular to the first direction.

12. The device of claim 11, wherein a first portion of the stem has a first diameter and a second portion of the stem has a second diameter, and wherein the second diameter is larger than the first diameter.

13. The device of claim 11, wherein a surface of the suction cup includes one or more aiming guides to provide an indication of an approximate center of the suction cup.

* * * * *